United States Patent
Roberts et al.

(10) Patent No.: US 10,966,838 B2
(45) Date of Patent: Apr. 6, 2021

(54) ARTICULATING KNEE SPACER AND METHOD OF MANUFACTURE

(71) Applicant: Oxford Performance Materials, Inc., South Windsor, CT (US)

(72) Inventors: Benjamin Roberts, South Windsor, CT (US); Andrus Maandi, South Windsor, CT (US); Severine Valdant Zygmont, South Windsor, CT (US); James Porteus, South Windsor, CT (US)

(73) Assignee: Oxford Performance Materials, Inc., S. Windsor, CT (US)

( * ) Notice: Subject to any disclaimer, the term of this patent is extended or adjusted under 35 U.S.C. 154(b) by 34 days.

(21) Appl. No.: 16/288,943

(22) Filed: Feb. 28, 2019

(65) Prior Publication Data
US 2020/0276024 A1    Sep. 3, 2020

(51) Int. Cl.
*A61F 2/38* (2006.01)
*A61F 2/30* (2006.01)

(52) U.S. Cl.
CPC .............. *A61F 2/389* (2013.01); *A61F 2/384* (2013.01); *A61F 2/3859* (2013.01); *A61F 2/3886* (2013.01); *A61F 2002/30624* (2013.01); *A61F 2002/30672* (2013.01)

(58) Field of Classification Search
CPC ... A61F 2/389; A61F 2/384; A61F 2002/4415
See application file for complete search history.

(56) References Cited

U.S. PATENT DOCUMENTS

| 3,065,205 A | 11/1962 | Bonner et al. | |
|---|---|---|---|
| 3,441,538 A | 4/1969 | Marks et al. | |
| 3,442,857 A | 5/1969 | Thornton et al. | |
| 3,516,966 A | 6/1970 | Berr et al. | |
| 3,696,446 A * | 10/1972 | Bousquet | A61F 2/3854 623/20.26 |
| 3,824,630 A * | 7/1974 | Johnston | A61F 2/385 623/20.22 |
| 4,092,740 A * | 6/1978 | Eshriqui | A61F 2/384 623/20.25 |

(Continued)

FOREIGN PATENT DOCUMENTS

| FR | 2913591 A1 | 9/2008 |
|---|---|---|
| WO | 2014100320 A1 | 6/2014 |

(Continued)

OTHER PUBLICATIONS

Parag Garg et al; "Antibiotic-impregnated articulating cement spacer for infected total knee arthroplasty", Nov.-Dec. 2011; Indian Journal of Orthopaedics 9 Pages.

(Continued)

*Primary Examiner* — Bruce E Snow
*Assistant Examiner* — Melissa A Hoban
(74) *Attorney, Agent, or Firm* — Welsh IP Law, LLC

(57) ABSTRACT

A joint implant for temporary or permanent use has a femoral component and tibial component. The femoral component has a base and rod extending therefrom and defines a pin. The tibial component has a base and rod extending therefrom and defines a bore in which the pin is seated so that the femoral component is rotatable relative to the tibial component.

17 Claims, 13 Drawing Sheets

(56) References Cited

U.S. PATENT DOCUMENTS

| | | | | |
|---|---|---|---|---|
| 4,242,758 | A | * | 1/1981 | Amis ................ A61B 17/1604 606/87 |
| 4,462,120 | A | | 7/1984 | Rambert et al. |
| 4,704,448 | A | | 11/1987 | Brugel |
| 4,816,556 | A | | 3/1989 | Gay et al. |
| 4,865,606 | A | * | 9/1989 | Rehder ................ A61F 2/384 623/20.23 |
| 5,413,607 | A | * | 5/1995 | Engelbrecht ....... A61B 17/1764 623/20.24 |
| 6,019,794 | A | | 2/2000 | Walker |
| 6,177,518 | B1 | | 1/2001 | Lahijani |
| 6,368,319 | B1 | * | 4/2002 | Schaefer ........... A61B 17/8635 411/412 |
| 6,447,549 | B1 | * | 9/2002 | Taft .......................... A61F 2/38 623/20.14 |
| 8,608,782 | B1 | * | 12/2013 | Rovner ................ A61B 17/708 606/264 |
| 8,845,691 | B2 | * | 9/2014 | Renaud .............. A61B 17/7034 606/264 |
| 8,998,996 | B2 | * | 4/2015 | James ................ A61F 2/30734 623/20.15 |
| 9,095,439 | B2 | * | 8/2015 | Lian ...................... A61F 2/4606 |
| 9,226,829 | B2 | | 1/2016 | Bartels et al. |
| 9,345,517 | B2 | * | 5/2016 | Zhang ............... A61B 17/7086 |
| 9,408,641 | B2 | * | 8/2016 | Zhang ............... A61B 17/7079 |
| 10,000,022 | B2 | | 6/2018 | DeFelice et al. |
| 10,085,839 | B2 | | 10/2018 | Wong et al. |
| 10,092,407 | B2 | | 10/2018 | Faccioli et al. |
| 10,603,077 | B2 | * | 3/2020 | Zhang ............... A61B 17/7001 |
| 2006/0229730 | A1 | * | 10/2006 | Railey ................ A61B 17/1775 623/21.18 |
| 2012/0065638 | A1 | | 3/2012 | Moore |
| 2015/0134068 | A1 | | 5/2015 | Leonard et al. |
| 2016/0206434 | A1 | | 7/2016 | Cappelletti |
| 2016/0296336 | A1 | * | 10/2016 | Maale .................. A61F 2/3804 |
| 2016/0367371 | A1 | | 12/2016 | de Beaubien et al. |
| 2017/0071745 | A1 | | 3/2017 | Magagnoli |
| 2017/0348110 | A1 | | 12/2017 | May et al. |
| 2018/0200922 | A1 | | 7/2018 | DeFelice et al. |

FOREIGN PATENT DOCUMENTS

| | | | |
|---|---|---|---|
| WO | 2016071938 | A1 | 5/2016 |
| WO | 2017199131 | A1 | 11/2017 |
| WO | 2018015878 | A1 | 1/2018 |

OTHER PUBLICATIONS

Susan M. Odum et al: "Irrigation and Debridement for Periprosthetic Infections", May 30, 2011; The Journal of Arthroplasty 1 Page.

Haddad et al: "Is single-stage revision according to a strict protocol effective in treatment of chronic knee arthroplasty infections?", Jan. 2015; 473 Clin Orthop Relat Res. 1 Page.

Byren et al: "One hundred and twelve infected arthroplasties treated with 'DAIR' (debridement, antibiotics and implant retention): antibiotic duration and outcome", Jun. 2009; 63 J. Antimicrob. Chemother. 1 Page.

Cheng et al: "Polymorphism and crystal structure identification in poly(aryl ether ketone ketone)s", Jan. 1996; Macromol Chem Phys 1 Page.

Luca Mazzucchelli et al: "The use of spacers (static and mobile) in infection knee arthroplasty", Sep. 22, 2015; Curr Rev Musculoskelet Med. Springer Science+Business Media New York 15 Pages.

Mortazavi et al: "Two-stage exchange arthroplasty for infected total knee arthroplasty: predictors of failure", Nov. 2011; 469 Clin Orthop Relate Res. 1 Page.

Rasmus Juul et al: "Use of a New Knee Prosthesis as an Articulating Spacer in Two-Stage Revision of Infected Total Knee Arthroplasty", Sep. 28, 20168; Korean Knee Society 9 Pages.

* cited by examiner

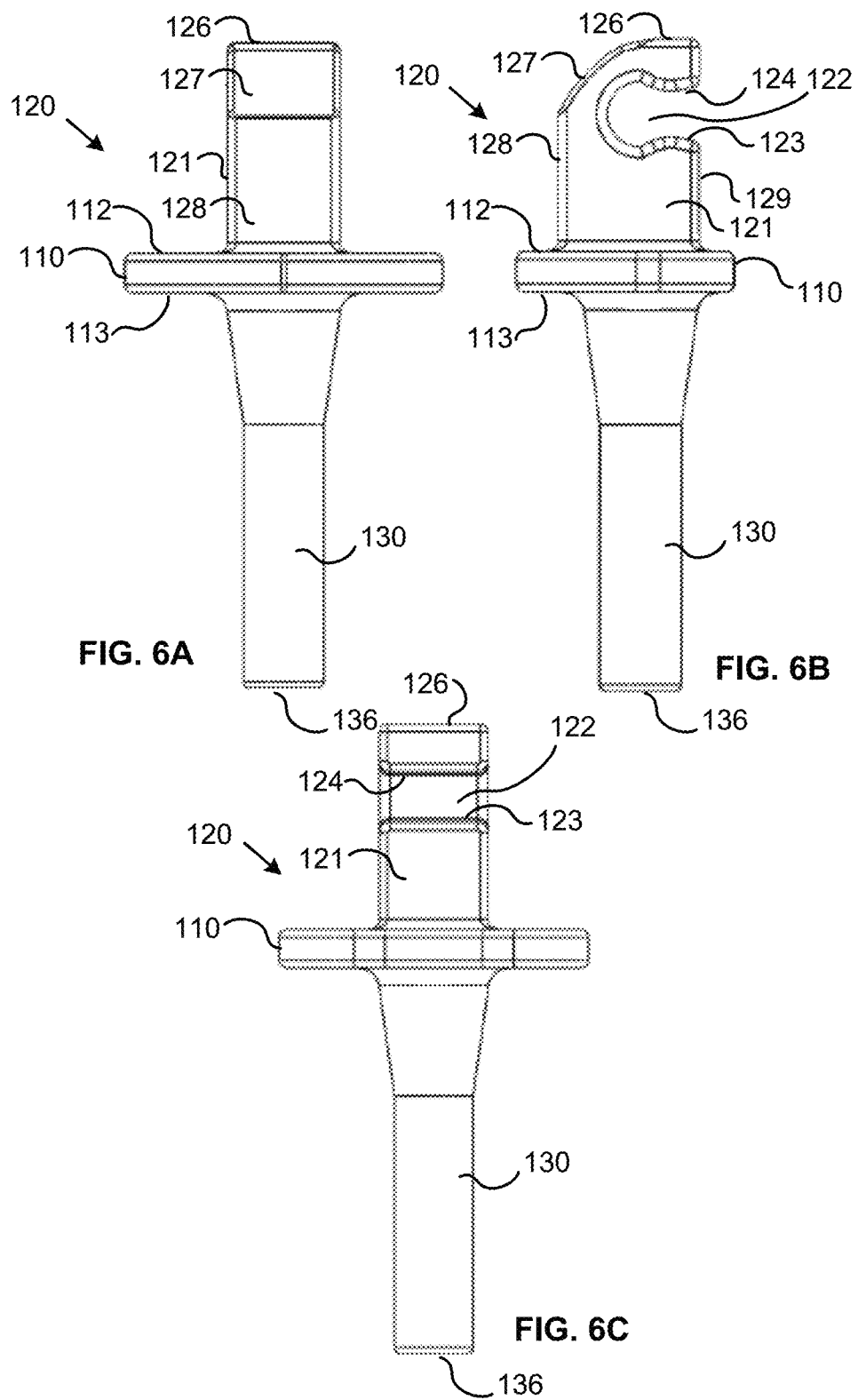

FIG. 7A
FIG. 7B
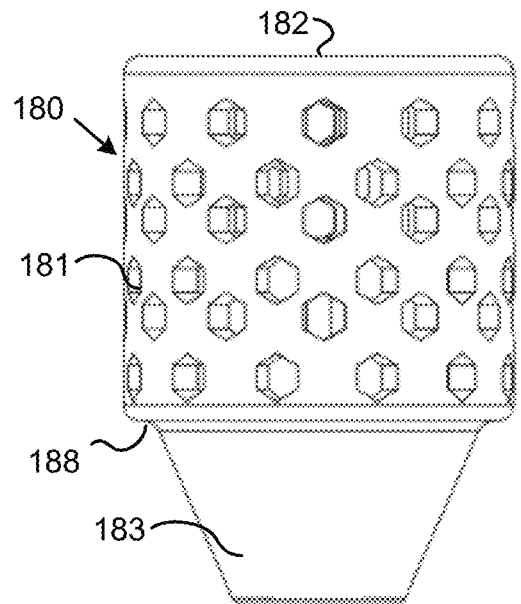
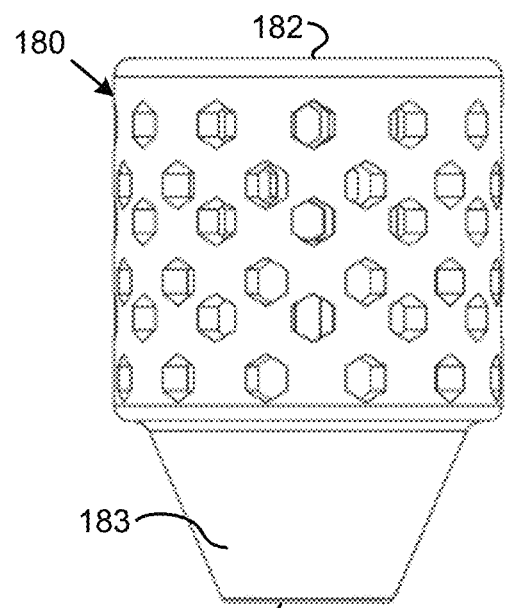
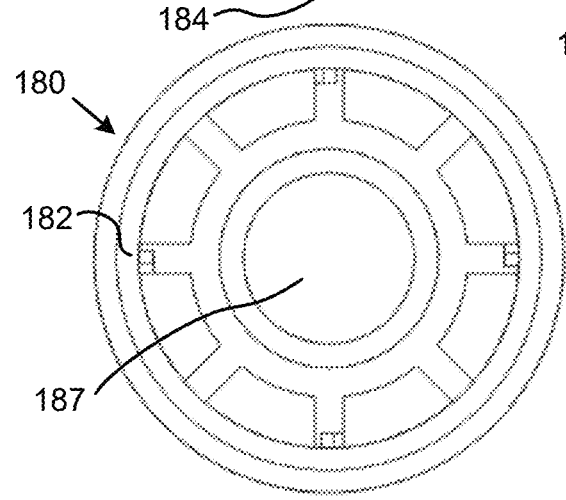
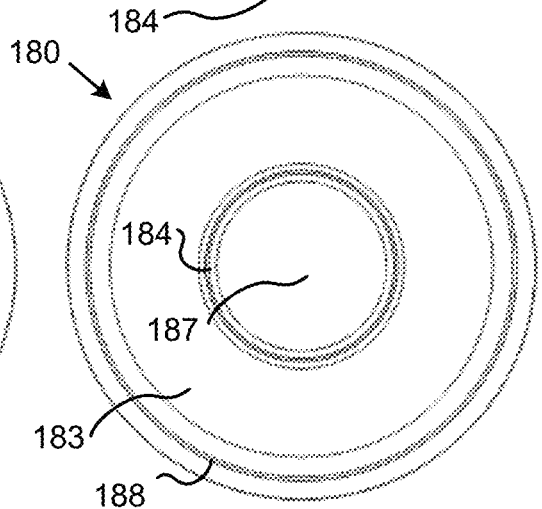
FIG. 7C
FIG. 7D

FIG. 9A
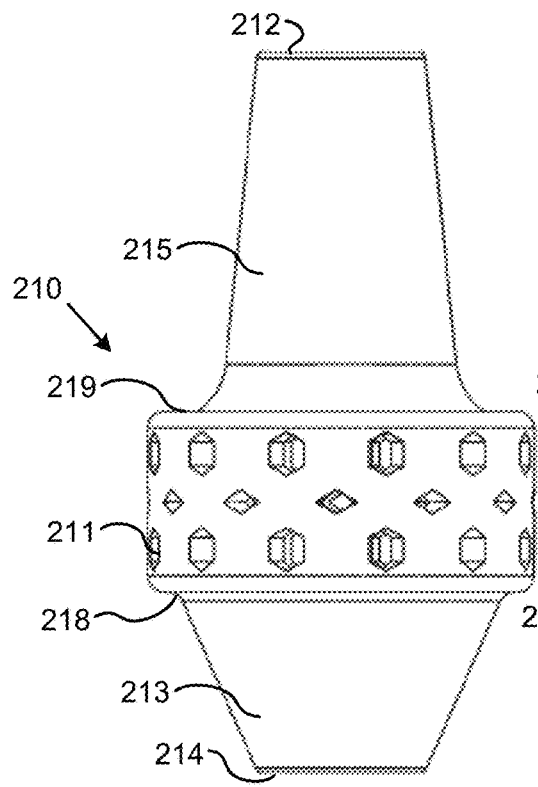
FIG. 9B
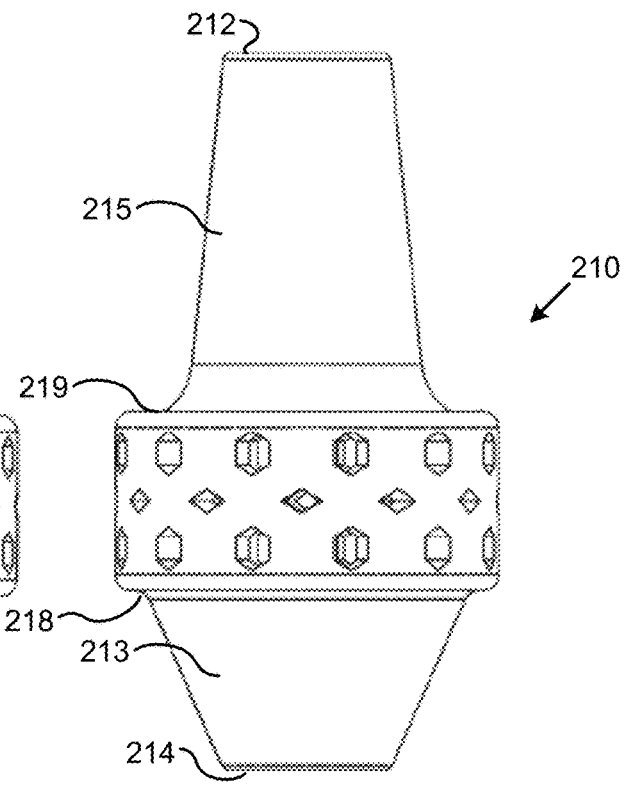
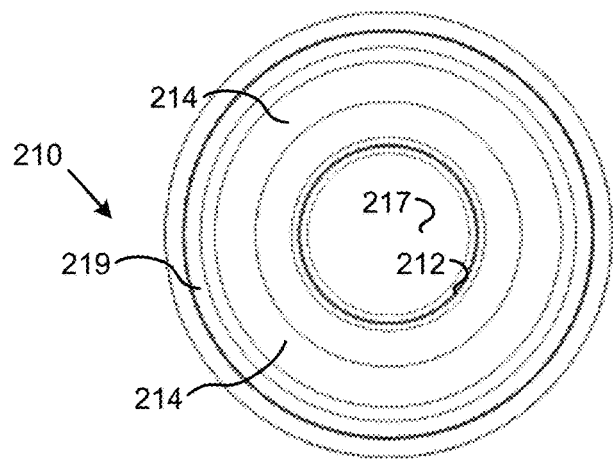
FIG. 9C
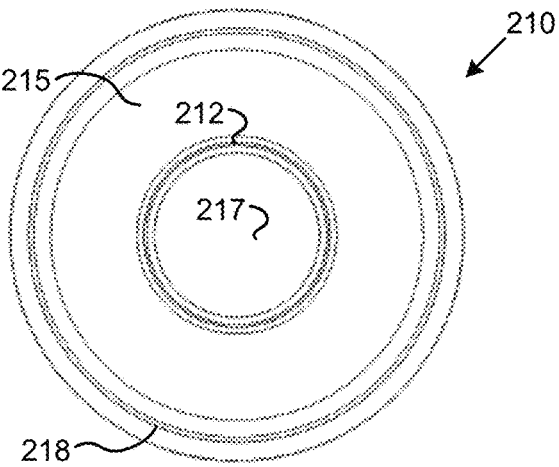
FIG. 9D

ARTICULATING KNEE SPACER AND METHOD OF MANUFACTURE

TECHNICAL FIELD

The present invention relates to a medical implant. More specifically, the present invention relates to a prosthetic knee implant for temporary or permanent use.

BACKGROUND

Though infection is an uncommon complication of arthroplasty, it may have devastating complications, both physical and economic, for a patient and for the healthcare system. Infection following total knee arthroplasty can be difficult to diagnose, and is often difficult to treat once it has been diagnosed. The revision procedure that must be undertaken once an infection has been identified typically involves a combination of surgical debridement to decrease the bacterial bioload as well as revision of one or more components of the prosthesis, and prolonged IV and/or oral antibiotics to eliminate the remaining bacteria. This will mean, for the patient, a longer operating time, greater blood loss, and more chance for other complications to arise, along with increases in the total number of hospitalizations of the patient, their duration of hospitalization, their total number of operations, their total hospital costs, and the total outpatient visits and charges that they must endure.

Several options exist for the treatment of an infected total knee arthroplasty. The first option is simple suppression of the infection with intravenous (IV) and/or oral antibiotics. This option is generally reserved for patients that are thought for any number of reasons to be unfit for surgery. As a general rule, simple IV and/or oral antibiotic treatment of an infected total knee arthroplasty without concomitant surgery is unlikely to result in eradication of an infection, but may suppress the infection such that it is minimally symptomatic.

The second option is a so-called "irrigation and debridement and polyethylene exchange." In this procedure, an open irrigation and debridement of the infected knee is undertaken, with concomitant removal of the spacer and placement of a new polyethylene spacer (a "polyethylene exchange"). In some instances, surgeons may elect to add dissolvable antibiotic beads to the knee at the time of surgery. Following this procedure, patients are generally placed on at least 6 weeks of IV antibiotics and may then be put on oral antibiotics for an indefinite period of time. The major advantage to this procedure is that it preserves the current metallic prosthesis, thus minimizing the morbidity of removing a well-fixed prosthesis. Removing a well-fixed prosthesis generally results in loss of variable amounts of native bone stock about the femur and tibia, which is of obvious detriment to the patient. The major disadvantage is that it may be difficult to eradicate the infection using this technique. The success rate for eradication of infection varies a great deal, from 31% to 75%. See, for example, S. M. Odum, T. K. Fehring, & A. V. Lombardi, et al., "Irrigation and debridement for periprosthetic infections: does the organism matter?" 26 J. Arthroplasty 6(suppl):114-118 (2011). See also, for example, I. Byren, P. Bejon, & B. L. Atkins, et al., "One hundred and twelve infected arthroplasties treated with 'DAIR' (debridement, antibiotics and implant retention): antibiotic duration and outcome," 63 J. Antimicrob. Chemother. 1264-1271 (2009).

The third option is a so-called "two-stage exchange." A two-stage exchange consists of two operations. In the first operation, the existing prosthesis and surrounding cement are both removed, a thorough irrigation and debridement is performed, and an antibiotic-eluting polymethylmethacrylate (PMMA) ("bone cement") temporary spacer is placed in place of the prosthesis. Multiple options for a replacement temporary spacer may exist for this procedure. For example, the temporary spacer may be a static spacer, which consists of a block of PMMA that spans the tibiofemoral space and as such holds the knee in a fixed extended position.

The temporary spacer may also be of the articulating variety; in this case, the femoral, tibial, and polyethylene parts of the knee are replaced with antibiotic-impregnated molded PMMA components, which may function as a temporary prosthesis, and which may temporarily elute a high, but ever diminishing concentration of antibiotics into the knee. This articulating device allows for some movement of the knee joint. There are several commercially available varieties of PMMA articulating spacers, some of which come pre-formed and pre-loaded with antibiotics. Additionally, each of these devices aim to temporarily replace the infected prosthesis. Following the first stage, in which the existing prosthesis is replaced with a temporary prosthesis, the patient is placed on at least 6 weeks of IV antibiotics. When the infection is thought to be eradicated, the second stage of the procedure is performed. In this stage, the PMMA spacer is removed, and replaced with a revision prosthesis. The advantage of a two-stage procedure is that it has a relatively high success rate, ranging from 72% to 93%. See, for example, S. M. Mortazavi, D. Vegari, A. Ho, B. Zmistowski, & J. Parvizi, "Two-stage exchange arthroplasty for infected total knee arthroplasty: predictors of failure," 469 Clin. Orthop. Relat. Res. 11:3049-54 (November 2011). See also F. S. Haddad, M. Sukeik, & S. Alazzawi, "Is single-stage revision according to a strict protocol effective in treatment of chronic knee arthroplasty infections?" 473 Clin. Orthop. Relat. Res. 1:8-14 (January 2015).

A disadvantage of a two-stage approach is that current temporary spacers have limited mobility and functionality, and thereby limit the mobility of the patient.

Another disadvantage of the two-stage approach is that in some cases, the patient is unfit for the second surgery. For example, in the case of elderly patients. In such cases, the temporary knee spacer becomes a permanent spacer. This is a disadvantage because of the limited mobility.

What is desired therefore is an improved temporary knee spacer that can also serve as a permanent knee spacer.

SUMMARY

The needs set forth herein as well as further and other needs and advantages are addressed by the present teachings, which illustrate solutions and advantages described below.

It is an objective of the present teachings to remedy the above drawbacks and issues associated with the prior art.

The present invention resides in one aspect in a prosthetic knee implant for temporary or permanent use. The implant comprises: a femoral component having a femoral base. A femoral rod extends along a longitudinal axis between a proximal end at the femoral base and a distal end. The base defines a pin that extends along a transverse axis and defines a substantially arcuate convex outer surface. The implant further includes a tibial component having a tibial base. A tibial rod extends along a longitudinal axis between a proximal end at the tibial base and a distal end. A support arm extends from the tibial base to a top surface at a distal end of the support arm. The support arm defines a bore that extends transversely through the support arm. The bore has a substantially concave arcuate bearing surface. The support arm further defines an opening along a length of the bore on a side surface of the support arm. A hinge assembly for pivotally mounting the femoral component to the tibial component comprises the pin seated in the bore of the support arm. The pin is receivable through the opening in the side surface of the support arm so that the femoral component and the tibial component are selectively connectable via the hinge assembly during a surgical procedure.

In yet a further embodiment of the present invention a width of the pin is greater than a width of the opening along the length of the bore.

In yet a further embodiment of the present invention the width of the pin and the width of the opening are selected to enable the surgeon to snap-fit the pin into the bore through the opening via an application of force. The geometry of the bore retains the pin.

In yet a further embodiment of the present invention an interface between the arcuate convex bearing surface defined by the pin and the arcuate concave bearing surface defined by the bore supports substantially all force between the femoral component and the tibial component.

In yet a further embodiment of the present invention the femoral component is rotatable relative to the tibial component about the hinge assembly along an arc of at least 60 degrees.

In yet a further embodiment of the present invention the implant includes a plurality of nesting spacers. Each of the spacers has a bore extending therethrough so that the spacer is receivable along on the femoral rod by passing the femoral rod through the bore.

In yet a further embodiment of the present invention the length of the spacers along the femoral rod may be varied by altering one or more the number of spacers or the type of spacers received along the femoral rod.

In yet a further embodiment of the present invention each of the plurality spacers includes a cone like structure at a proximal end for nesting with an adjacent spacer.

In yet a further embodiment of the present invention the plurality of spacers comprises an end spacer, the end spacer having a second cone structure at its distal end.

In yet a further embodiment of the present invention each of the plurality of spacers defines an interior cavity having a plurality of openings in a surface thereof.

In yet a further embodiment of the present invention the implant comprises sintered PEKK.

BRIEF DESCRIPTION OF THE DRAWINGS

FIG. 6A is a front view of the tibial component of the implant shown in FIG. 2

FIG. 6B is a side view of the tibial component shown in FIG. 6A.

FIG. 6C is a rear view of the tibial component shown in FIG. 6A.

FIG. 7A is a front view of a spacer of the implant shown in FIG.

FIG. 7B is a side view of the spacer shown in FIG. 7A.

FIG. 7C is a top view of the spacer shown in FIG. 7A.

FIG. 7D is a bottom view of the spacer shown in FIG. 7A.

FIG. 9A is a front view of a spacer of the implant shown in FIG. 2.

FIG. 9B is a side view of the spacer shown in FIG. 9A.

FIG. 9C is a top view of the spacer shown in FIG. 9A.

FIG. 9D is a bottom view of the spacer shown in FIG. 9A.

DETAILED DESCRIPTION

Figure 1:
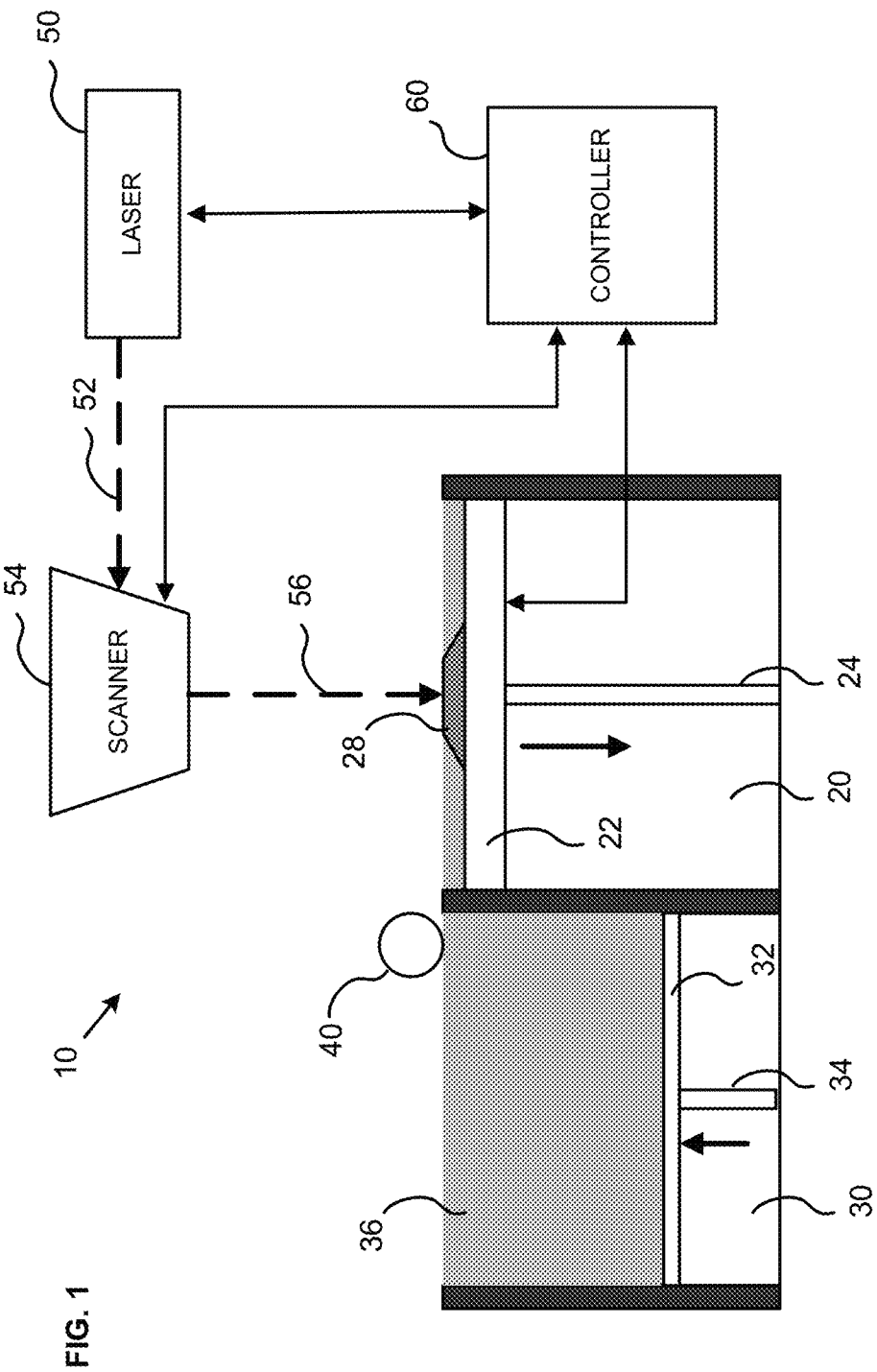
FIG. 1 is an illustration of a laser sintering machine in accordance with one embodiment of the present invention.

The present disclosure describes aspects of the present invention with reference to the exemplary embodiments illustrated in the drawings; however, aspects of the present invention are not limited to the exemplary embodiments illustrated in the drawings. It will be apparent to those of ordinary skill in the art that aspects of the present invention include many more embodiments. Accordingly, aspects of the present invention are not to be restricted in light of the exemplary embodiments illustrated in the drawings. It will also be apparent to those of ordinary skill in the art that variations and modifications can be made without departing from the true scope of the present disclosure. For example, in some instances, one or more features disclosed in connection with one embodiment can be used alone or in combination with one or more features of one or more other embodiments.

The present invention relates to joint replacements manufactured from polymer powders by laser sintering. Although laser sintering of polymer powders is disclosed, the present invention is not limited in this regard and a person of skill in and familiar with this disclosure will understand that additional techniques and materials may be used.

One such class of polymer powders is polyaryletherketone ("PAEK") polymers. PAEKs are of interest in the SLS process because parts that have been manufactured from PAEK powder or PAEK granulates are characterized by a low flammability, a good biocompatibility, and a high resistance against hydrolysis and radiation. The thermal resistance at elevated temperatures as well as the chemical resistance distinguishes PAEK powders from ordinary plastic powders. A PAEK polymer powder may be a powder from the group consisting of polyetheretherketone ("PEEK"), polyetherketoneketone ("PEKK"), polyetherketone ("PEK"), polyetheretherketoneketone ("PEEKK") or polyetherketoneetherketoneketone ("PEKEKK").

PEKKs are well-known in the art and can be prepared using any suitable polymerization technique, including the methods described in the following patents, each of which is incorporated herein by reference in its entirety for all purposes: U.S. Pat. Nos. 3,065,205; 3,441,538; 3,442,857; 3,516,966; 4,704,448; 4,816,556; and 6,177,518. PEKK polymers differ from the general class of PAEK polymers in that they often include, as repeating units, two different isomeric forms of ketone-ketone. These repeating units can be represented by the following Formulas I and II:

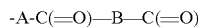   I

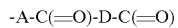   II where A is a p,p'-Ph-O-Ph-group, Ph is a phenylene radical, B is p-phenylene, and D is m-phenylene. The Formula I:Formula II isomer ratio, commonly referred to as the T:I ratio, in the PEKK is selected so as to vary the total crystallinity of the polymer. The T:I ratio is commonly varied from 50:50 to 90:10, and in some embodiments 60:40 to 80:20. A higher T:I ratio such as, 80:20, provides a higher degree of crystallinity as compared to a lower T:I ratio, such as 60:40.

The crystal structure, polymorphism, and morphology of homopolymers of PEKK have been studied and have been reported in, for example, Cheng, Z. D. et al, "Polymorphism and crystal structure identification in poly(aryl ether ketone ketone)s," Macromol. Chem. Phys. 197, 185-213 (1996), the disclosure of which is hereby incorporated by reference in its entirety. This article studied PEKK homopolymers having all para-phenylene linkages [PEKK(T)], one meta-phenylene linkage [PEKK(I)], or alternating T and I isomers [PEKK(T/I)]. PEKK(T) and PEKK(T/I) show crystalline polymorphism depending upon the crystallization conditions and methods.

In PEKK(T), two crystalline forms, forms I and II, are observed. Form I can be produced when samples are crystallized from melting at low supercooling, while Form II is typically found via solvent-induced crystallization or by cold-crystallization from the glassy state at relatively high supercooling. PEKK(I) possesses only one crystal unit cell which belongs to the same category as the Form I structure in PEKK(T). The c-axis dimension of the unit cell has been determined as three phenylenes having a zig-zag conformation, with the meta-phenylene lying on the backbone plane. PEKK(T/I) shows crystalline forms I and II (as in the case of PEKK(T)) and also shows, under certain conditions, a form III.

Suitable PEKKs are available from several commercial sources under various brand names. For example, polyetherketoneketones are sold under the brand name OXPEKK® polymers by Oxford Performance Materials, South Windsor, Conn. Polyetherketoneketone polymers are also manufactured and supplied by Arkema. In addition to using polymers with a specific T:I ratio, mixtures of polyetherketoneketones may be employed.

The powders used in these applications are produced by a variety of processes such as grinding, air milling, spray drying, freeze-drying, or direct melt processing to fine powders. The heat treatment can be accomplished before or after the powders are produced, but if treated prior to forming the powders, the temperature of the powder forming process must be regulated to not significantly reduce the melting temperature or the quantity of the crystallinity formed in the heat treatment process.

In regard to the embodiment using PEKK powder, a raw PEKK flake is provided. The raw PEKK flake is commercially available from companies such as Arkema, Inc. of King of Prussia, Pa., and Cytec Industries Inc. of Woodland Park, N.J.

A heat treatment step is optionally performed on the PEKK flake. The heat-treatment process is the subject of US patent application Ser. No. 15/872,478 filed on Jan. 16, 2018 by Hexcel Corporation and titled "Polymer Powder and Method of Using the Same." The disclosure of that reference is hereby incorporated by reference. After the optional heating step, a grinding or milling step is performed that involves grinding the raw PEKK flake to form what will hereinafter be referred to as the "PEKK powder." The grinding step can be performed using known grinding techniques performed by companies such as Aveka, Inc. of Woodbury, Minn. Upon completion of the grinding step, the particles of the PEKK powder are significantly smaller (i.e., several degrees of magnitude smaller) than the particles of the raw PEKK. The particles of the PEKK powder are more consistent and regular in shape as compared to the particles of the raw PEKK; however, the particles of the PEKK powder are still irregularly-shaped in comparison to the spherical-shaped particles. A person of ordinary skill in the art and familiar with this disclosure will understand that the grinding may also be referred to as pulverization, milling, or jet milling. In addition, a person of ordinary skill in the art and familiar with this disclosure will understand that it may also be employed with other polymer powders, including those in the PAEK family.

The raw PEKK flake is ground into a PEKK powder comprising a plurality of PEKK particles. The PEKK particles range in size from less than 10 μm to about 200 μm. A person of ordinary skill in the art and familiar with this disclosure will understand that the particle size range will vary based on the type of polymer being milled and the specific parameters of the milling process. After the milling, an air classification method may be used to separate fine particles from the milled PEKK powder. It is known in the art that it is necessary to reduce or eliminate particles having a diameter below a cut-off point, for example 30 μm, as it has been found that particles in this range prevent use of the powder in the LS process. For example, International Patent Application WO2014100320 discloses such a method for preparing powders for use in selective laser sintering. It is understood in the art that parts cannot be manufactured in the SLS process from a powder wherein the fine particles have not been sieved from the powder. Such an unsieved powder causes pilling, sticking, and other forms of fouling in the powder application steps of the SLS process, and further results in curling and premature melting that inhibit use of such powders in the SLS process.

In some embodiments of the present invention a recycled polymer powder is used. Recycled PEKK material has previously been used in an SLS process but not formed into an object. The recycle process is the subject of U.S. Pat. No. 10,000,022 to Hexcel Corporation and titled "method for processing PAEK and articles manufactured from the same." The disclosure of that reference is hereby incorporated by reference.

According to one embodiment of the present invention, in reference to FIG. 1, a laser sinter ("LS") system 10 in accordance with the present invention is illustrated. The system 10 includes a first chamber 20 having an actuatable piston 24 deposed therein. A bed 22 is deposed at an end of the piston 24. It should be understood that the term bed may refer to the physical structure supported on the piston or the uppermost layer of powder deposed thereon.

The temperature of the bed 22 can be variably controlled via a controller 60 in communication with heating elements (not shown) in or around the bed 22. Furthermore, the LS system 10 according to the invention may include a heating device (not shown) above the bed 22, which preheats a newly applied powder layer up to a working temperature below a temperature at which the solidification of the powder material occurs. The heating device may be a radiative heating device (e.g., one or more radiant heaters) which can introduce heat energy into the newly applied powder layer in a large area by emitting electromagnetic radiation.

A second chamber 30 is adjacent to the first chamber 20. The second chamber 30 includes a table surface 32 disposed on an end of a piston 34 deposed therein. A powder 36 for use in the LS system 10 is stored in the second chamber 30 prior to the sintering step. It will be understood to a person of ordinary skill in the art and familiar with this disclosure that while a specific embodiment of a LS system is disclosed, the present invention is not limited thereto, and different known LS systems may be employed in the practice of the present invention.

During operation of the LS system 10, a spreader 40 translates across a top surface of the first chamber 20, evenly distributing a layer of powder 36 across onto either the top surface of the bed 22 or the material previously deposed on the bed 22. The LS system 10 preheats the powder material 36 deposed on the bed 22 to a temperature proximate to a melting point of the powder. Typically, a layer of powder is spread to have a thickness of 125 µm, however the thickness of the layer of powder can be increased or decreased depending on the specific LS process and within the limits of the LS system.

A laser 50 and a scanning device 54 are deposed above the bed 22. The laser 50 transmits a beam 52 to the scanner 54, which then distributes a laser beam 56 across the layer of powder 36 deposed on the bed 22 in accordance with build data. The build data comprises a computer-aided design ("CAD") file having a geometric description of the object that is being built. The laser selectively fuses powder material by scanning cross-sections generated from a three-dimensional digital description of the part on the surface of the bed having a layer of the powder material deposed thereon. The laser 50 and the scanner 54 are in communication with the controller 60. After a cross-section is scanned, the bed 22 is lowered by one-layer thickness (illustrated by the downward arrow), a new layer of powdered material is deposed on the bed 22 via the spreader 40, and the bed 22 is rescanned by the laser. This process is repeated until a build 28 is completed. During this process, the piston 34 in the second chamber is incrementally raised (illustrated by the upward arrow) to ensure that there is a sufficient supply of powder 36.

Parts made from the SLS process have a dimensional tolerance of between 0.2 mm and 0.5 mm plus or minus a specified dimensional value as set forth in the CAD file having a geometric description of the object. It will be understood to a person of ordinary skill in the art and familiar with this invention that the term CAD file having a geometric description of the object includes any set of electronic instructions for the SLS machine to print an object with a specified geometry.

The ±0.2 to ±0.5 mm dimensional tolerance associated with SLS is caused by several different factors associated with SLS. First, as the object cools after the printing job it typically contracts and shrinks. It is possible to account for this shrinkage by adjusting the geometric description of the object in the CAD file. Nevertheless, some variance in the dimensional tolerance is likely. A second cause of the dimensional tolerance is that the polymer powder in the build chamber adjacent to sintered object may inadvertently adhere to the surface of the object as a result of incidental melting or incidental particle adhesion due to the thermal conductivity of the adjacent sintering source. This effect is seen on the up skin and down skin surfaces, and on the z-plane surfaces. Another factor that affects the dimensional tolerance associated with the SLS of polymers is the subsequent buildup of layers that form the objects.

One embodiment of an implant 100 in accordance with the present invention in shown in FIGS. 2-13. The implant may be referred to as a knee spacer, temporary spacer, or permanent spacer. Although the knee joint is used as an example in this disclosure, the present invention is not limited in this regard and that spacer may be used in other types of joints.

The implant 100 is a long segmental hinged cemented knee spacer and functions as a temporary or permanent knee joint prosthesis. The spacer includes a femoral component 160 and a tibial component 120. The femoral component 160 and the tibial component 120 are connected via a hinge assembly so that the tibial component is rotatable relative to the femoral component about an axis of rotation. The implant 100 comprises a plurality of nesting spacers 166, 180, 190, 210 that allow adjusting the length of the implant 100 inserted into the femoral cavity. In the embodiment disclosed, the implant 100 is manufactured via an additive manufacturing comprising selective laser sintering of polyetherketoneketone (PEKK). The implant 100 allows for partial weight bearing and a natural range of motion for patients undergoing a two-stage revision procedure. The implant 100 also maintains a patient's soft tissue and joint space, preventing further complications like muscular contraction. The implant 100 is designed to be used with bone cement (loaded with antibiotics) to help secure the implant and to deliver local antimicrobial antibiotic therapy, as is standard for infection treatment.

In reference to the FIGS, the implant 100 includes a femoral component 160 and a tibial component 120.

The femoral component 160 has a femoral base 150. In the embodiment disclosed, the femoral base 150 defines a substantially circular outer surface in a cross-sectional plane and it extends along a transverse length so that the base 150 is substantially cylindrical. The shape of the outer surface of the base 150 is configured to facilitate rotation of the femoral component 160 about the tibial component 120 inside the anatomy of the recipient. A person of skill in the art and familiar with this disclosure will understand that different contours and shapes of the base may be employed with the present invention.

The femoral component 160 includes a femoral rod 170 that extends along a longitudinal axis between a proximal end at a top surface 154 of the femoral base 150 and a distal end 176. The femoral rod 170 is substantially linear and rigid.

The femoral component 160 includes a first spacer 166 that is integral with the base 150. The spacer 166 extends from the top surface 154 of the base 150 along the longitudinal axis. The first spacer 166 defines a bore that extends substantially therethrough in the direction of the longitudinal axis. A top surface 168 defines an opening 169 to the bore in the spacer 166. As show in FIG. 5C, the femoral rod 170 passes through the opening 169 in the top surface 168 of the first spacer 166 and extends to the top surface 154 of the base 150. In other embodiments of the present invention, the first spacer is not integral with the base, but rather a separate component that can be added at the discretion of the surgeon.

The base 150 of the femoral component 160 further defines a pin 152 proximate to a bottom 155 of the base 150. The pin 152 extends along a transverse axis. In the embodiment disclosed in the FIGS., the pin 152 defines a substantially arcuate convex outer surface along a length of the pin 152. The pin 152 has a constant diameter across its length. The pin 152 is connected to the base 150 on its ends. The base 150 defines a substantially hollow area 151 above the pin 152. The pin 152 forms the first part of a hinge assembly for pivotally mounting the femoral component 160 on the tibial component 120.

Figure 5A:
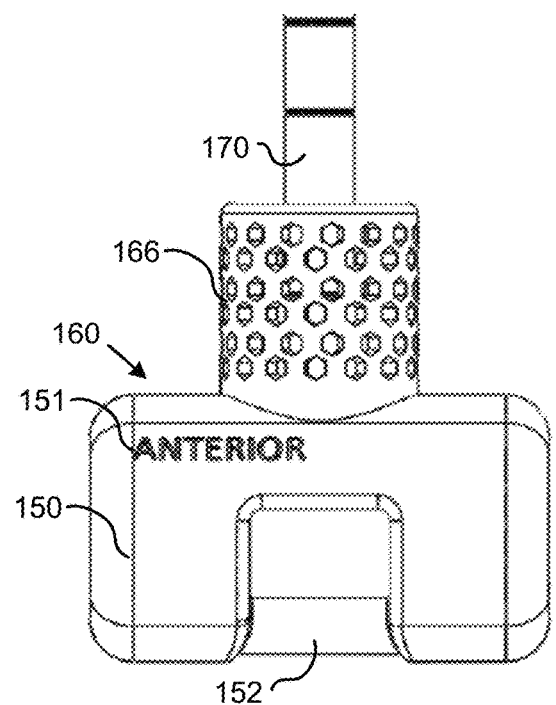
FIG. 5A is a front view of a femoral component of the implant shown in FIG. 2.
Figure 5B:
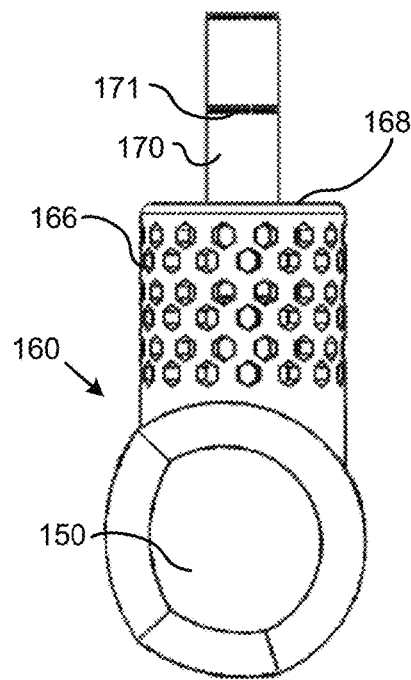
FIG. 5B is a side view of the femoral component shown in FIG. 5A.
Figure 5C:
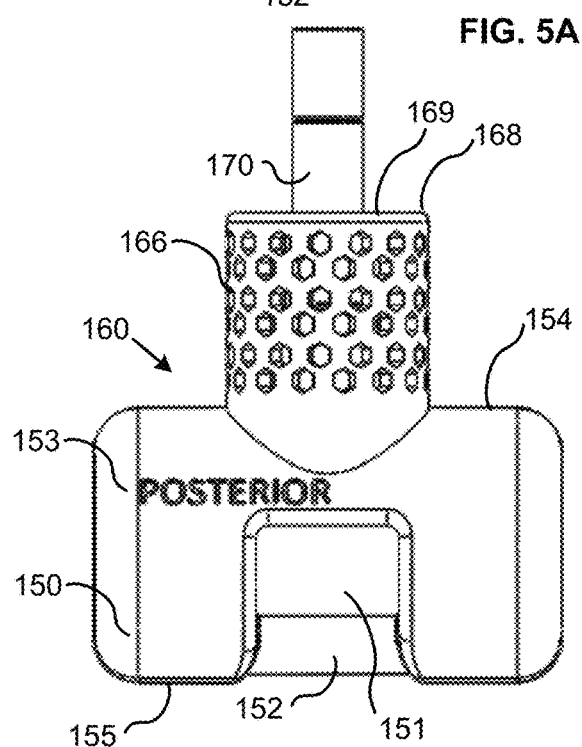
FIG. 5C is a rear view of the femoral component shown in FIG. 5A.
Figure 5D:
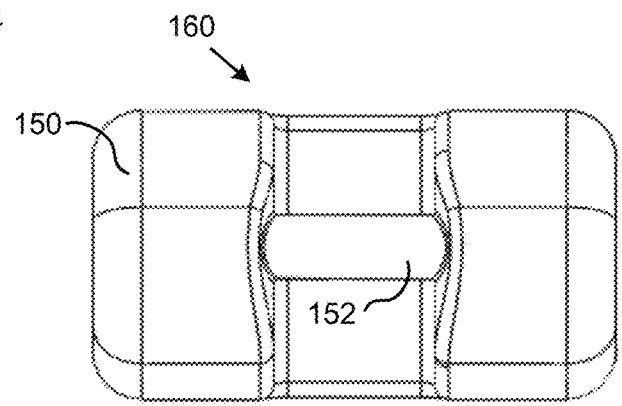
FIG. 5D is a bottom view of the femoral component shown in FIG. 5A.
Figure 8A:
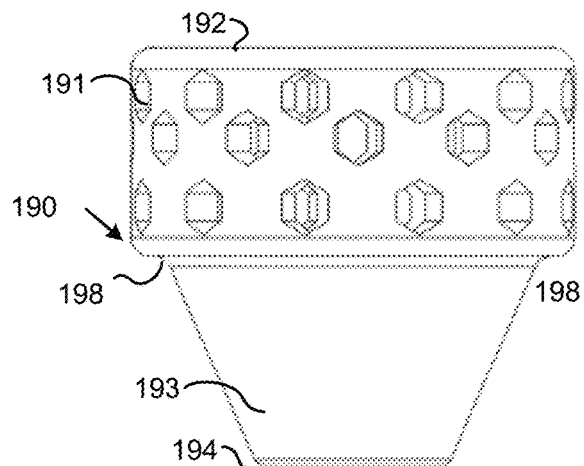
FIG. 8A is a front view of a spacer of the implant shown in FIG. 2.
Figure 8B:
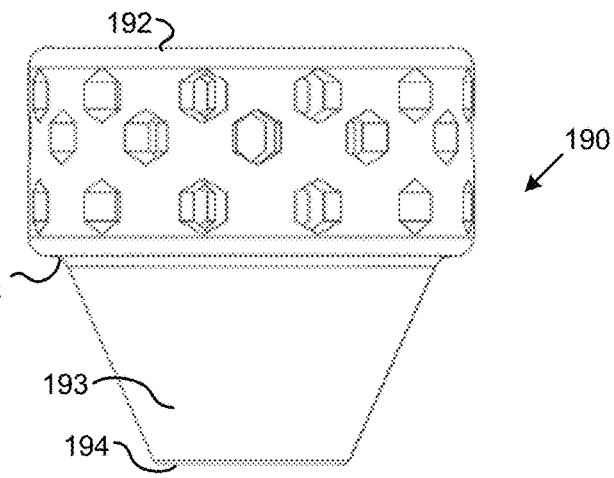
FIG. 8B is a side view of the spacer shown in FIG. 8A.
Figure 8C:
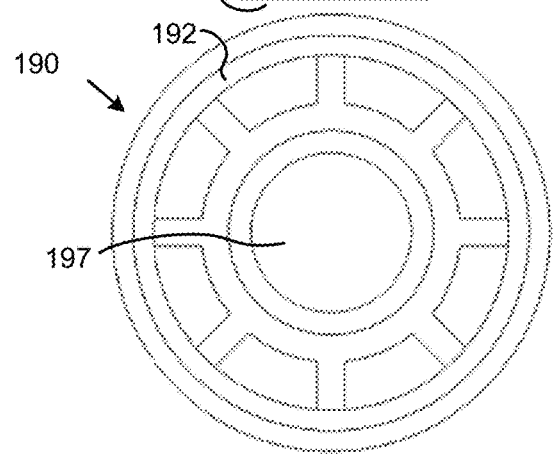
FIG. 8C is a top view of the spacer shown in FIG. 8A.
Figure 8D:
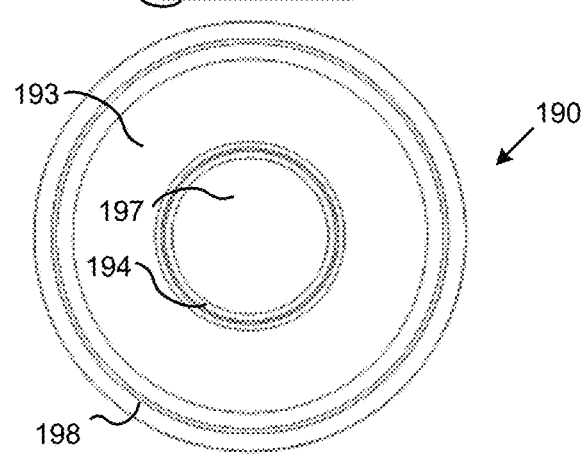
FIG. 8D is a bottom view of the spacer shown in FIG. 8A.

In reference to FIG. 5A, a surface of the base 150 defines a relief pattern that spells ANTERIOR 151. Likewise, in reference to FIG. 5B, a surface of the base on the opposing side defines a relief pattern that spells POSTERIOR 153. The indications 151, 153 are formed during the additive manufacturing process and enable a person to distinguish between the front and back of the implant 100 to ensure that it properly used. A person of skill in the art and familiar with this disclosure will understand that the relief indications 151, 153 are optional and are not required to practice the disclosed invention. Furthermore, that person will understand that a different type of indication may be used. In the embodiment disclosed, the implant is symmetrical about a mid-plane that vertically bisects the implant 100. Therefore, the implant 100 may be used in either a left leg or a right leg. In some embodiments, a different shape is provided for an implant in the left leg and the right leg. These embodiments may include an indication of a lateral and medial side via a relief pattern or some other means to provide an indication to the surgeon.

The implant 100 in accordance with the invention includes a tibial component 120. The tibial component 120 includes a tibial base 110. The tibial base 110 is substantially planar and has a top surface 112 and a bottom surface 113. The tibial base 110 extends in a plane perpendicular to a longitudinal axis of the tibial component. A tibial rod 130 extends along a longitudinal axis between a proximal end at the bottom surface 113 of the tibial base 110 and a distal end 136. In the embodiment disclosed, the tibial rod 130 defines a circular cross section in a plane perpendicular to the longitudinal axis of the tibial rod 130.

Figure 11:
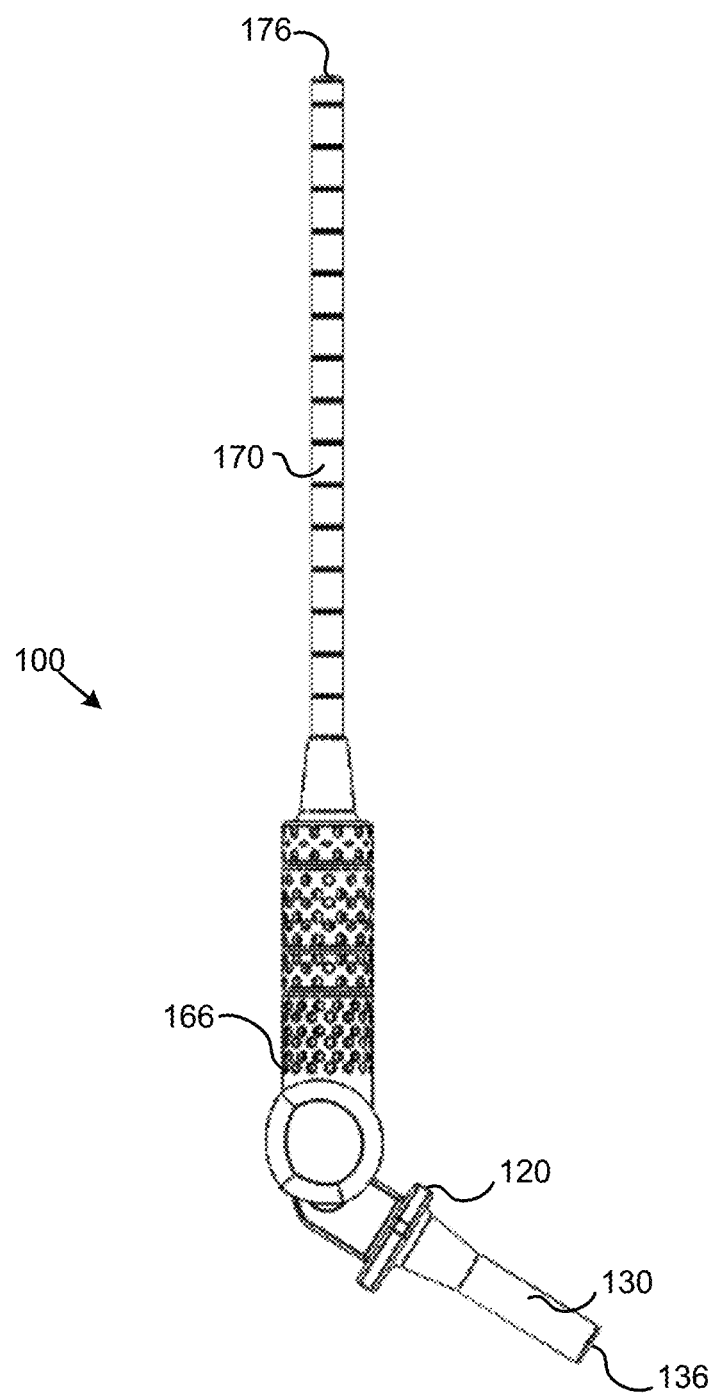
FIG. 11 is a side view of the implant shown in FIG. 2.
Figure 12:
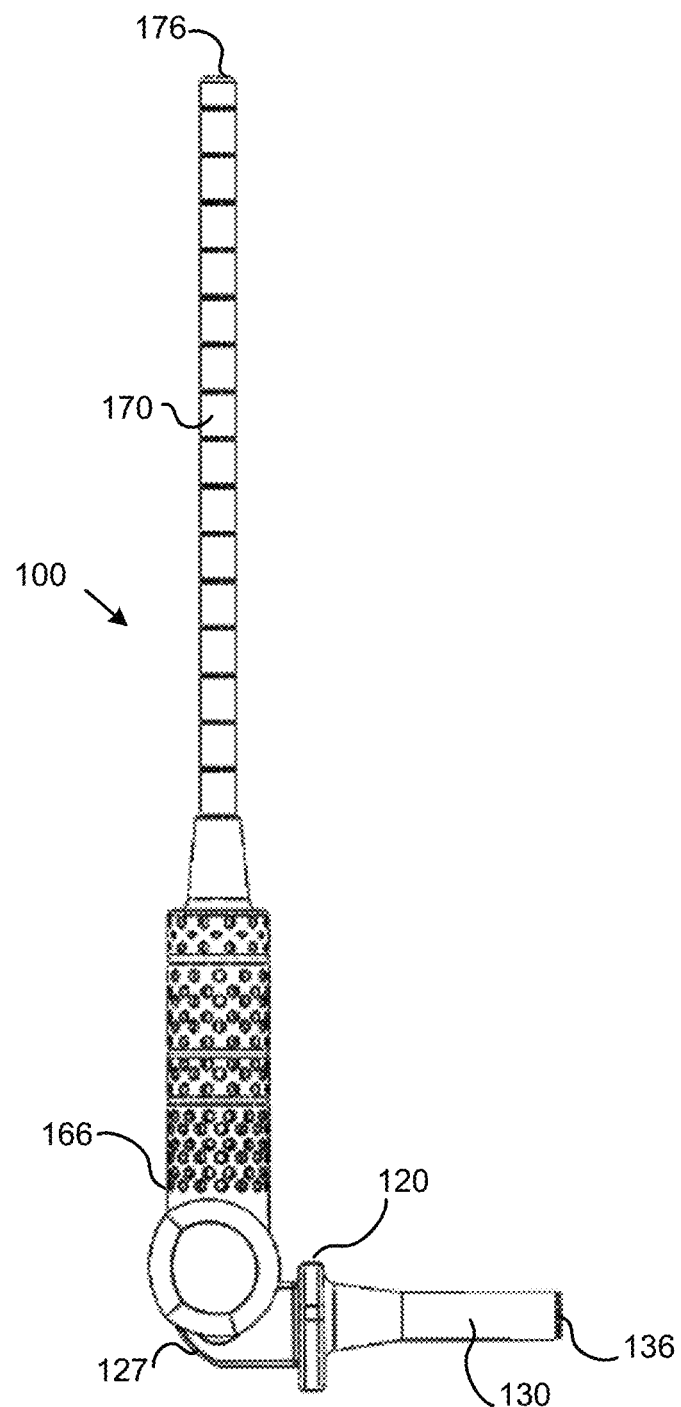
FIG. 12 is a side view of the implant shown in FIG. 2.
Figure 13:
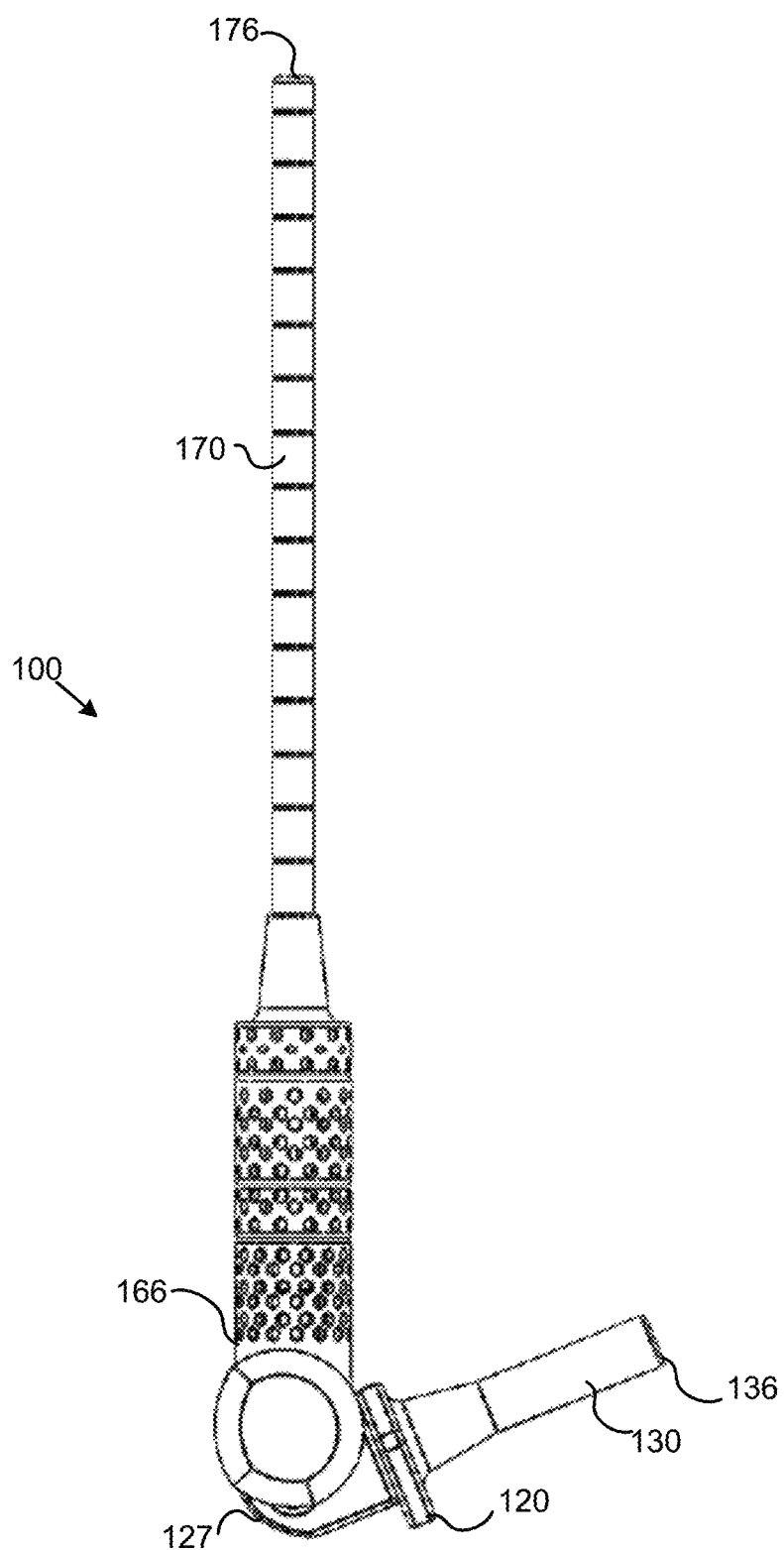
FIG. 13 is a side view of the implant shown in FIG. 2.

The tibial component 120 further includes a support arm 121 that extends upward from a top surface 113 of the tibial base 110 to a top surface 126 at a distal end of the support arm 121. The support arm 121 is configured to receive the pin 152 so that the tibial component 120 is rotatable relative to the femoral component 160. The support arm 121 is substantially rectangular in cross-section plane perpendicular to its longitudinal axis. The top surface 126 is substantially flat and extends in a plane parallel to the tibia base 110. A front face 128 of the support arm 121 and the top surface 126 extends in perpendicular planes. The support arm includes a transition section 127 that extends between the front face 128 and the upper surface 126. The transition section 127 forms an approximate 45 degree angle with the top surface and with the front face. The transition section 127 ensures the top area 126 of the support arm aligns with an outer surface of the femoral component 160, and more specifically the base 150, when the femoral component 160 is rotated at an angle relative to the tibial component 120. For example, as shown in FIGS. 11, 12, and 13.

The support arm 121 defines a bore 122 for receiving the pin 152. The bore 122 extends transversely through the support arm 121 from a left side to a right side and defines openings in the surface of the support arm 121 at each of the left side and right side. The bore 122 defines a substantially arcuate bearing surface that extends along the length of the bore 122. The support arm 121 further defines an opening in a rear surface 129 of the support arm 121. The opening extends between a bottom edge 123 in the rear surface 129 and a top edge 124 in the rear surface.

The pin 152 is receivable in the bore 122 through the opening 123, 124 so that the pin 152 is rotatable in the bore 122. In this manner, the pin 152 and the bore 122 define a hinge assembly for pivotally mounting the femoral component 160 to the tibial component 120. In the embodiment disclosed, a width of the pin 152 is greater that a width of the opening 123, 124 at its narrowest point. The diameter of the pin 152 is 9 mm. The width of opening between 123 and 124 at the outer surface is 10.5 mm. The width of this opening narrows to 8.35 mm at its narrowest point that is radially inward from the outer surface as shown in FIG. 6B. Thus, the diameter of the pin 152 is greater than the narrowest point of the opening between 123 and 124. The funnel type expansion of the opening to 10.5 mm from the narrowest point to the outer surface guides the pin 152 into position and aids with assembly during the surgical procedure. The specific design feature requires the surgeon apply a force between the tibial component 120 and the formal component 160, thereby elastically increasing the width of the opening so that the pin 152 is received in the bore 122. After application of the force and seating, the pin 152 is seated in the bore and retained therein via a more narrow opening. In this manner, the surgeon can separately install the femoral component 160 and the tibial component 120 and then snap-fit them together during the surgical procedure. The surgeon can separate the two components 120, 160 by applying a substantially equivalent opposite force. The strength of the snap fit and the its retention ability can be varied by adjusting the width of the opening and width/diameter of the pin 152. The retention strength of the seat can be further varied by factors including, but not limited to the elastic modulus of the building material and the geometry of the support arm. In the embodiment disclosed, the width of the opening at its most narrow point is about 0.65 mm less than the diameter of the pin 152. A person of ordinary skill in the art and familiar with the disclosure, will understand that different dimensions may by employed with the present invention depending on the geometry of the design and properties of the utilized material. Furthermore, the person will understand that the diameter of the pin 152 may be less than the width of the opening at its narrowest point while still being capable of practicing the present invention.

The hinge assembly defined by the pin 152 and the bore 122 is unique in the context of implants for at least the reason that interface of the bearing surface of the bore 122 and the bearing surface of the pin 152 is the only support interface between the femoral component 160 and the tibial component 120.

In the embodiment disclosed, the opening 123,124 is one a side surface of the support arm 121, as opposed to the top surface 126. This configuration improves the rotation by increasing the surface of the bearing area defined by the bore 122. It further helps retain the pin 152 in the bore 122 when the femoral component 160 and tibial component 120 are subject to tensile forces. In some embodiments of the present invention, the base 110 and upper surface thereof 112 interface with the body 130 of the tibial component 120 to limit rotation thereof relative to the tibial. In this manner, the design of the of geometry of the implant can be used to set a limit on the amount of rotation.

Figure 4:
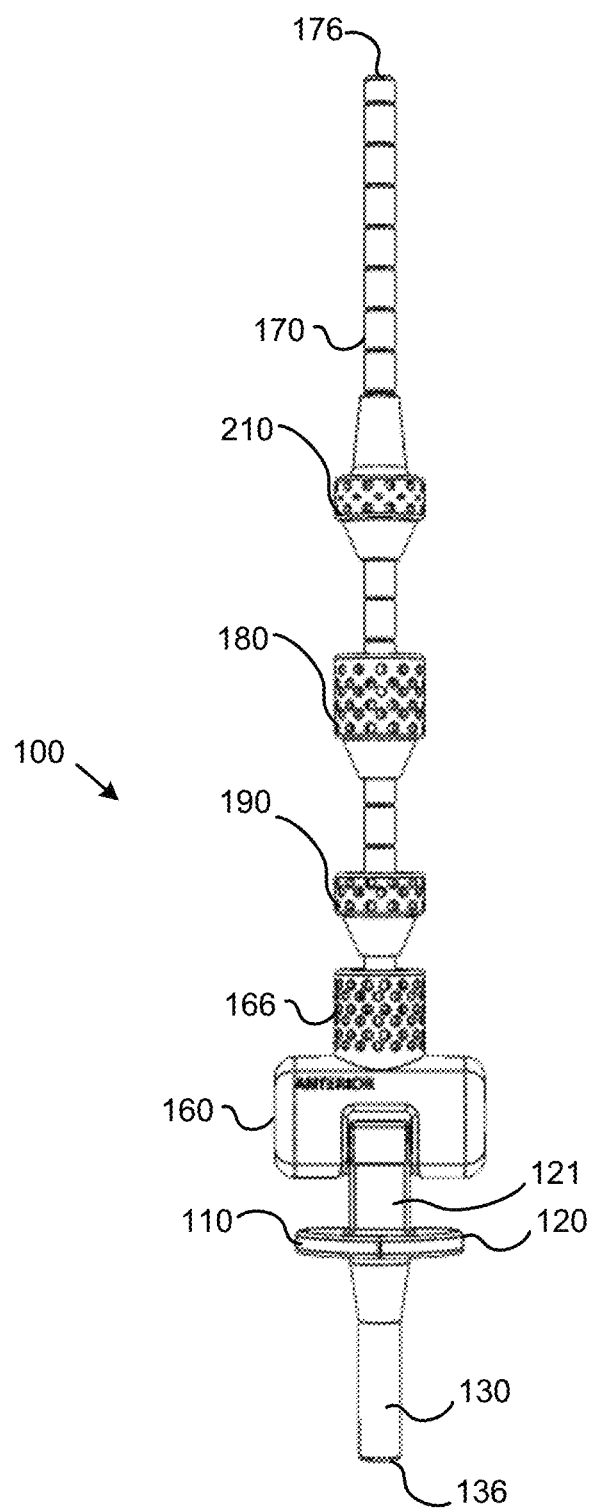
FIG. 4 is a front view of the implant shown in FIG. 2.

In reference to FIG. 4, the implant 100 includes a plurality of nesting spacers 166, 190, 180, and 210. The surgeon can selectively vary the height of intramedullary fixation by varying the height of the nesting sections by selecting a different combination and number of the nesting spacers 190, 180, 210. In the embodiment disclosed, the first spacer 166 is permanently fixed to the body 150 of the femoral component 160.

In reference to FIGS. 7A-7D a 30 mm femoral spacer 180 is shown. Note that the 30 mm section refers to the length of the cylindrical body and does not include the cone. In the embodiment disclosed, the spacer 180 is formed by SLS of PEKK, although other materials and techniques could be used. The spacer 180 comprises a hollow cylindrical body that extends from a first end 182 to a second end 188. The cylindrical body is hollow and defines a plurality of through holes 181 between the cavity and the outside. In the embodiment disclosed, the through holes are hexagonal in cross-section, although the present invention is not limited in this regard and other shapes may be employed with the present invention. The spacer 180 includes a rim 182 at the first end and a rim 188 at the opposing end. The rims 182, 188 provide an interface surface for the nest spacers 166, 180, 190, 210.

The spacer 180 further includes a hollow cone 183 extending from the second end proximate the rim 188 to a truncated apex 184 of the cone 183. The spacer 180 has a circular opening 187 at the truncated apex 184 of the cone 183. The diameter of the opening 187 is greater than the outside dimeter of the femoral rod 170 so that the spacer is in slideable engagement with the femoral rod 170.

Figure 2:
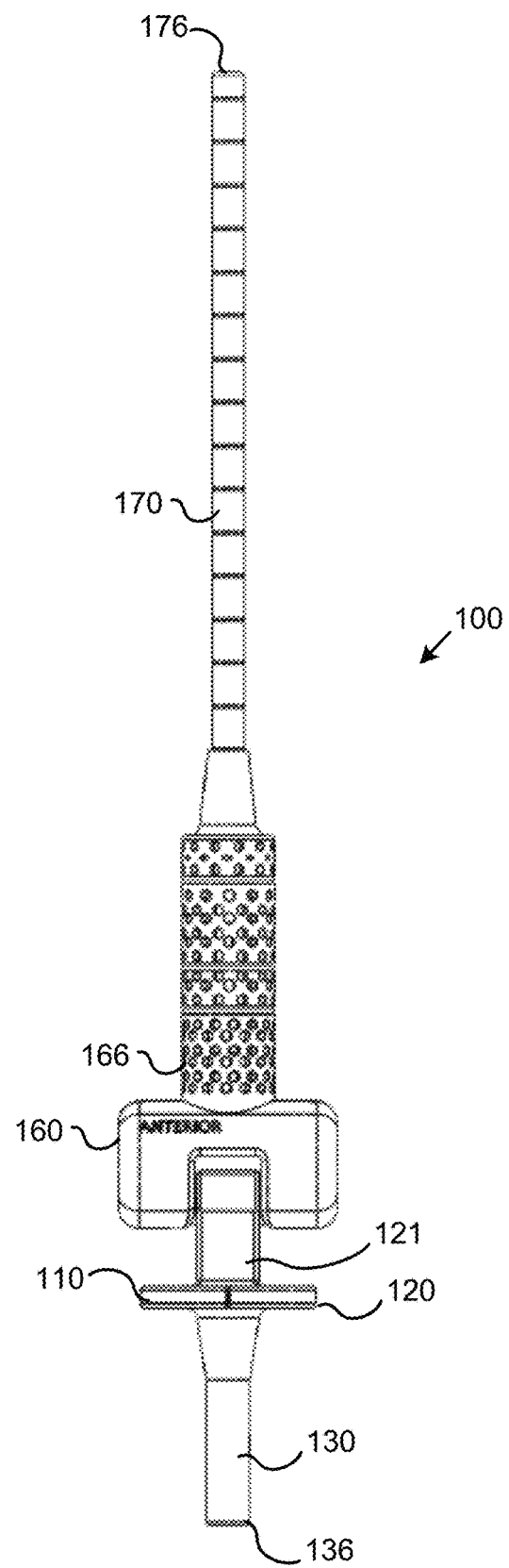
FIG. 2 is a front view of an implant in accordance with one embodiment of the present invention.
Figure 3:
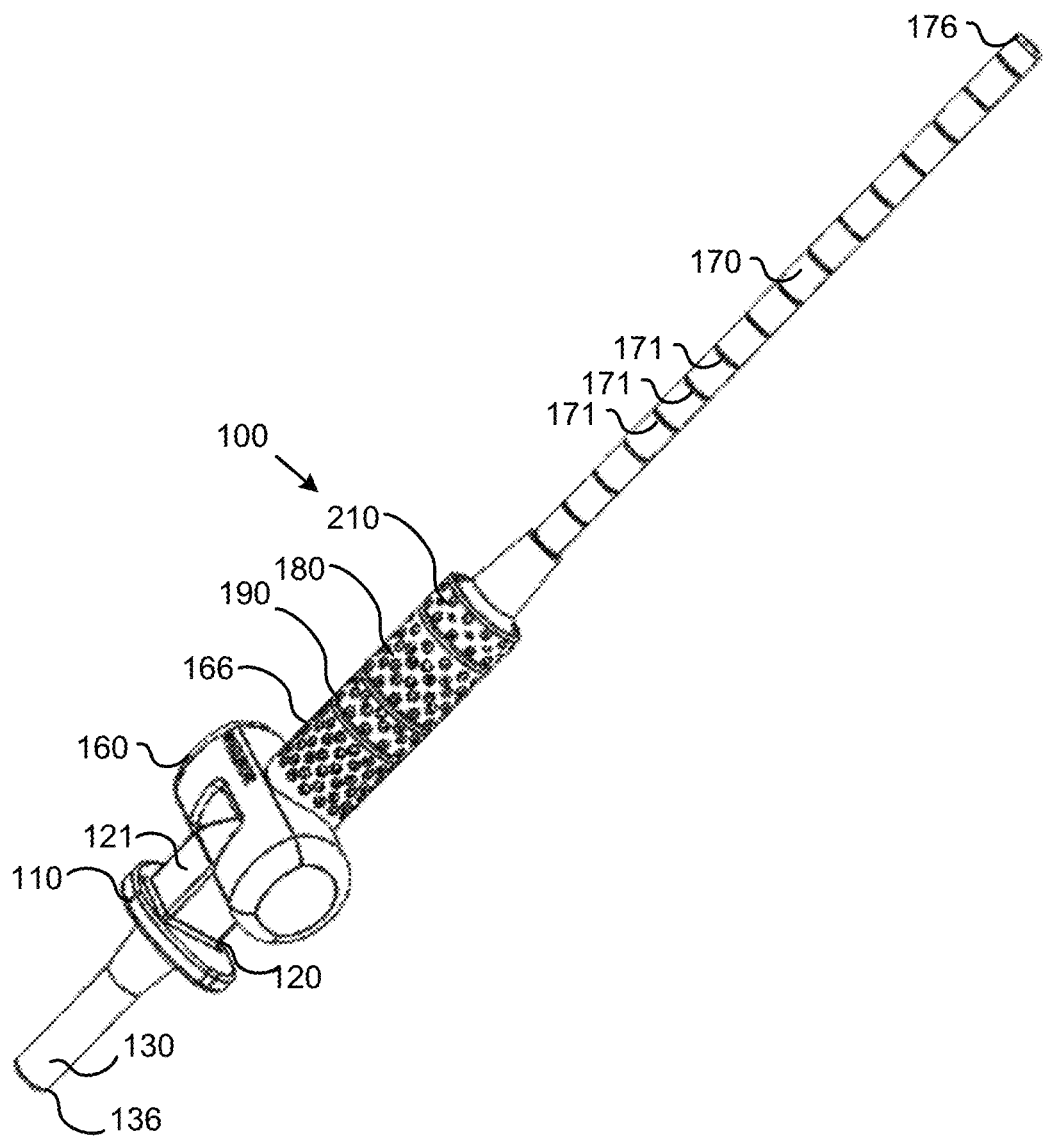
FIG. 3 is a perspective view of the implant shown in FIG. 2.

In reference to FIG. 4, the cone is received in hollow cavity of an adjacent spacer, thereby nesting and forming a stack of spacers, as shown in FIG. 2. The spacer 180 can be stacked on the femoral component (around the femoral rod) to add extra length to the femoral construct. The 30 mm femoral spacer is designed with hexagonal through-holes 181 to allow for filling and packing of bone cement. The cone 181 nests inside the first spacer 166 on the femoral base 150 or another spacer 190, 180 to add stability to the construct.

In reference to FIGS. 8A-8D a 15 mm femoral spacer 190 is shown. Note that the 15 mm dimension refers to the length of the cylindrical body and does not include the height of the cone. In the embodiment disclosed, the spacer 190 is formed by SLS of PEKK, although other materials and techniques may be used. The spacer 190 comprises a hollow cylindrical body that extends from a first end 192 to a second end 198. The body 190 defines a plurality of through holes 191 extending between the cavity and the outside. In the embodiment disclosed, the through holes are hexagonal in cross-section, although the present invention is not limited in this regard and other shapes may be employed with the present invention. The spacer 190 includes a rim 192 at the first end and a rim 198 at the opposing end. The rims 192, 198 provide an interface surface for the nesting spacers 166, 180, 190, 210.

The spacer 190 further includes a hollow cone 193 extending from the second end proximate the rim 198 to a truncated apex 194 of the cone 193. The spacer 190 has a circular opening 197 at the truncated apex 194 of the cone 193. The diameter of the opening 197 is greater than the outside dimeter of the femoral rod 170 so that the spacer is slideably engagement with the femoral rod 170.

In reference to FIG. 4, the cone is received in hollow cavity of an adjacent spacer, thereby nesting and forming a stack of spacers, as shown in FIG. 2. The spacer 180 can be stacked on the femoral component (around the femoral rod) to add extra length to the femoral construct. The 15 mm femoral spacer 190 is designed with hexagonal through-holes 181 to allow for filling and packing of bone cement. The cone 191 nests inside the first spacer 166 on the femoral base 150 or another spacer 190, 180 to add stability to the construct.

In reference to FIGS. 9A-9D a 15 mm femoral spacer 210 is shown. Note that the 15 mm dimension refers to the length of the cylindrical body and does not include the height of the cones. This spacer 210 is intended to be the last (or only) spacer stacked on the femoral component 160 around the femoral rod 170. The 15 mm spacer cap 210 is designed with hexagonal and diamond through-holes to allow for filling and packing of bone cement. The bottom cone 213 stacks inside the femoral component 166 or another spacer 180, 190 and the top cone portion 215 inserts into the patient's femoral canal to add stability and a smooth transition of the cemented construct to the patient's bone.

In the embodiment disclosed, the spacer 210 is formed by SLS of PEKK, although other materials and techniques may be used. The spacer 210 comprises a hollow cylindrical body that extends from a first end 219 to a second end 218. The body 210 defines a plurality of through holes 211 extending between the cavity and the outside. In the embodiment disclosed, the through holes are hexagonal in cross-section, although the present invention is not limited in this regard and other shapes may be employed with the present invention.

The spacer 210 further includes a hollow cone 213 extending from the second end proximate the rim 218 to a truncated apex 214 of the cone 213. The spacer 210 has a circular opening 217 at the truncated apex 214 of the cone 213. The diameter of the opening 217 is greater than the outside dimeter of the femoral rod 170 so that the spacer is slideably engagement with the femoral rod 170.

The spacer 210 further includes a hollow cone 215 extending from the first end proximate the rim 219 to a truncated apex 212 of the cone 215. The spacer 210 has a circular opening 217 at the truncated apex 212 of the cone 215. The diameter of the opening 217 is greater than the outside diameter of the femoral rod 170 so that the spacer is in slideable engagement with the femoral rod 170. The cone 215 is configured to interface with the patient bone.

The femoral rod 170 includes a plurality of notches 171 formed in a surface thereof. In the embodiment disclosed, the notches 171 are spaced at 15 mm intervals. During a surgical procedure, the surgeon cuts the femoral rod 170 to a desired length for the patient. The notches help the surgeon to initiate a cut of the femoral rod 170. In addition, the notches serve as a handy reference indicator. A person of skill in the art and familiar with this disclosure will understand that the present invention can be practiced without the notches.

Figure 10:
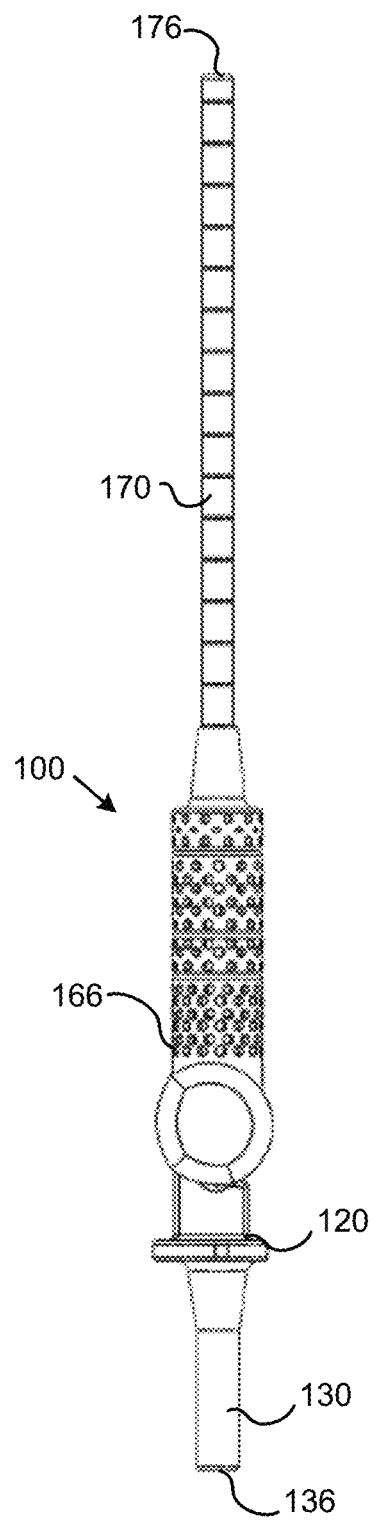
FIG. 10 is a side view of the implant shown in FIG. 2.

In reference to FIGS. 10-13, the implant 100 is shown at different points of articulation. In FIG. 10, the longitudinal axis of the femoral rod 170 is aligned with the longitudinal axis of the tibial rod 130. In FIG. 11, the femoral rod 170 forms an angle of about 45 degrees with the tibial rod 130. In FIG. 12, the femoral rod 170 forms an angle of about 90 degrees with the tibial rod 130. In FIG. 13, the femoral rod 170 forms an angle of about 120 degrees with the tibial rod 130. In reference to the FIGS, particularly 12-13, the effect of the transition section 127 is shown to create a smooth outer surface in the articulated implant.

The implant 100 in accordance with the present invention has applications in primary long segment reconstructions that become infected or in situations where a temporary spacer is required. Often times, known temporary knee spacer solutions consist of rods and cement, which locks the patient's leg straight for the duration of the first stage of treatment before placement of a permanent implant. The implant 100 in accordance with the present invention is intended to allow for partial weight bearing and a natural range of motion through the hinged components 120, 160. The spacer 100 is intended to mimic the permanent implant, providing the surgeon an easy-to-assemble device and providing the patient a high standard of care.

The knee spacer 100 may be provided in separate, unassembled components for use in the operating room. A description of the typical surgical technique with the implant 100 is provided. A person of skill in the art and familiar with this disclosure will understand that the steps and technique may vary based on the implant embodiments, the patient, the surgeon, among other factors.

In this embodiment, the surgeon first resects the infected bone or infected implant from the knee joint and cleans the joint/tissue space. Once the site is ready for the temporary knee spacer 100, the surgeon determines the length of the femoral rod 170 needed for implantation. At this point, the surgeon would test fit the femoral component 160 and any spacers 180, 190, 210, as well as the tibial component 120, without snapping the components together.

After measuring and test fitting the components, the femoral rod is cut to an appropriate length, leaving a portion of the stem on the proximal end of the femoral component 160 for insertion into the patient's femoral canal. The femoral canal may also be reamed out to ensure fit of the stem and spacer cap component. The tibial plateau may be cut to ensure proper implant spacing and the tibial canal may also be reamed out to ensure fit of the tibial stem.

At this point, the femoral component 160 would be packed with bone cement (loaded with surgeon preference of antibiotics) and subsequently, spacer components would be added and also filled with bone cement. Bone cement should fill the cavities in the spacers until it presses out from the through-holes 189, 191, 211. The cement can then be worked around the cylindrical portion of the distal femoral component and the spacer cap piece before being inserted into the patient's femur.

Quickly after insertion of the femoral component 160, the tibial component 120 can be inserted with bone cement under the flat tibial plate and around the tibial stem.

Once both components are inserted, they are snapped together. Working quickly, any adjustments are made to ensure straight alignment of the joint before the bone cement cures. Once positioned, the joint is set and the bone cement is allowed to cure. After confirming satisfactory range of motion and implant placement, the wound can be closed per standard techniques.

While the present teachings have been described above in terms of specific embodiments, it is to be understood that they are not limited to those disclosed embodiments. Many modifications and other embodiments will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. A prosthetic knee implant for temporary or permanent use, the implant comprising:
    a femoral component having a femoral base, a femoral rod extending along a longitudinal axis between a proximal end at the femoral base and a distal end, the base defining a pin that extends along a transverse axis and defines a substantially arcuate convex outer surface;
    a tibial component having a tibial base, a tibial rod extending along a longitudinal axis between a proximal end at the tibial base and a distal end, a support arm extending from the tibial base to a top surface at a distal end of the support arm, the support arm defining a bore extending transversely through the support arm, the bore having a substantially concave arcuate bearing surface, the support arm further defining an opening along a length of the bore on a side surface of the support arm;
    a hinge assembly pivotally mounting the femoral component to the tibial component, the hinge assembly comprising the pin seated in the bore of the support arm,
    wherein the pin is receivable through the opening in the side surface of the support arm so that the femoral component and the tibial component are selectively connectable via the hinge assembly during a surgical procedure,
    wherein a width of the pin is greater than a smallest width of the opening along the length of the bore.

2. The implant of claim 1, wherein the width of the pin and the width of the opening are selected to enable the surgeon to snap-fit the pin into the bore through the opening via an application of force,
    and wherein a geometry of the bore retains the pin.

3. The implant of claim 1, wherein an interface between the arcuate convex bearing surface defined by the pin and the arcuate concave bearing surface defined by the bore supports substantially all force between the femoral component and the tibial component.

4. The implant of claim 3, wherein the femoral component is rotatable relative to the tibial component about the hinge assembly along an arc of at least 60 degrees.

5. The implant of claim 4 further comprising:
    a plurality of nesting spacers, each of the spacers having a bore extending therethrough so that the spacer is receivable along on the femoral rod by passing the femoral rod through the bore.

6. The implant of claim 5 wherein the length of the spacers along the femoral rod may be varied by altering one or more of the number of spacers or the type of spacers received along the femoral rod.

7. The implant of claim 6, wherein each of the plurality spacers includes a cone like structure at a proximal end for nesting with an adjacent spacer.

8. The implant of claim 7, wherein the plurality of spacers comprises an end spacer, the end spacer having a second cone structure at its distal.

9. The implant of claim 8, wherein each of the plurality of spacers defines an interior cavity having a plurality of openings in a surface thereof.

10. The implant of claim 9 comprising one or more of PEKK and PEEK.

11. The implant of claim 10 comprising sintered PEKK.

12. A joint implant for temporary or permanent use, the implant comprising:
    a femoral component having a femoral base, a femoral rod extending along a longitudinal axis between a proximal end at the femoral base and a distal end, the base comprising a pin that extends along a transverse axis and defines a substantially arcuate convex outer surface;
    a tibial component having a tibial base, a tibial rod extending along a longitudinal axis between a proximal end at the tibial base and a distal end, a support arm extending from the tibial base to a top surface at a distal end of the support arm, the support arm defining a bore extending transversely through the support arm, the bore having a substantially concave arcuate bearing surface;

wherein the pin is seated in the bore of the support arm to form a hinge assembly so that the femoral component and the tibial component are selectively connectable via the hinge assembly during a surgical procedure, wherein in the support arm comprises an opening along the length of the bore to receive the pin in the bore, wherein the width of the opening is less than a width of the pin by a length x.

13. The joint implant of claim 12, wherein x is selected so that an application force by human adult hands can snap-fit the pin into the bore.

14. The joint implant of claim 12, wherein x is at least 0.5 mm.

15. The joint implant of claim 12, wherein the tibial component comprises a tibial base being substantially planar and perpendicular to the longitudinal axis of the tibial rod, and wherein the support arm is substantially rectangular in a cross-section perpendicular to the longitudinal axis, and wherein the top surface is substantially flat and extends in a plane parallel to the tibial base; wherein a front face of the support arm and the top surface extend in perpendicular planes, and wherein the support arm further comprises a transition section that extends between the front face and the top surface.

16. The joint implant of claim 15, wherein the transition section intersects the longitudinal axis at an angle of between 30 and 60 degrees.

17. The joint implant of claim 16, further comprising:
a plurality of nesting spacers, each of the spacers having a bore extending therethrough so that the spacer is receivable along the femoral rod by passing the femoral rod through the bore.

* * * * *

UNITED STATES PATENT AND TRADEMARK OFFICE
CERTIFICATE OF CORRECTION

| | | |
|---|---|---|
| PATENT NO. | : 10,966,838 B2 | Page 1 of 1 |
| APPLICATION NO. | : 16/288943 | |
| DATED | : April 6, 2021 | |
| INVENTOR(S) | : Benjamin Roberts et al. | |

It is certified that error appears in the above-identified patent and that said Letters Patent is hereby corrected as shown below:

In the Specification

On Column 1, Line 9 the following text should be added:
"FEDERAL SUPPORT CLAUSE
This invention was made with government support under Grant Number R03AR066366 awarded by the National Institutes of Health. The Government has certain rights in the invention."

Signed and Sealed this
Eleventh Day of April, 2023

*Katherine Kelly Vidal*

Katherine Kelly Vidal
*Director of the United States Patent and Trademark Office*